(12) United States Patent
Albrecht et al.

(10) Patent No.: US 8,709,449 B2
(45) Date of Patent: Apr. 29, 2014

(54) METHODS AND COMPOSITIONS FOR IMPROVING PHOTODYNAMIC THERAPY THROUGH ADMINISTRATION OF LIPIDS

(75) Inventors: Volker Albrecht, Jena (DE); Susanna Gräfe, Jena (DE)

(73) Assignee: Biolitec Pharma Marketing Ltd, F.T. Labuan (MY)

( * ) Notice: Subject to any disclaimer, the term of this patent is extended or adjusted under 35 U.S.C. 154(b) by 1544 days.

(21) Appl. No.: 11/055,923

(22) Filed: Feb. 10, 2005

(65) Prior Publication Data

US 2005/0215524 A1    Sep. 29, 2005

Related U.S. Application Data

(60) Provisional application No. 60/543,984, filed on Feb. 12, 2004.

(51) Int. Cl.
*B32B 27/30* (2006.01)
*C08K 5/04* (2006.01)
*C08K 5/09* (2006.01)

(52) U.S. Cl.
USPC ............ 424/400; 514/78; 514/185; 514/410; 604/20

(58) Field of Classification Search
None
See application file for complete search history.

(56) References Cited

U.S. PATENT DOCUMENTS

| | | | | |
|---|---|---|---|---|
| 5,616,342 | A | * | 4/1997 | Lyons ............................ 424/450 |
| 6,074,666 | A | * | 6/2000 | Desai et al. .................... 424/450 |
| 6,103,706 | A | * | 8/2000 | Ben-Hur ......................... 514/63 |
| 2002/0058643 | A1 | * | 5/2002 | Cherian et al. ................. 514/78 |

OTHER PUBLICATIONS

Fukuda et al., Potential of liposome-entrapped aminolevulinic acid in cancer therapy Effect of prior injection of empty liposomes and different routes of administration, Cancer Journal (1192), 5(5), 295-9.*

Fukuda et al "Potential of liposomes-entrapped aminolevulic acid in liposomes and different routes of administration", Cancer Journal (1192), vol. 5, Issue 5, pp. 295-299.*

Gregoriadis "Liposome Technology interactions of liposomes with the biological milieu", vol. III, 2nd Edition, 1993.*

* cited by examiner

*Primary Examiner* — Wu-Cheng Winston Shen
*Assistant Examiner* — Jean Cornet
(74) *Attorney, Agent, or Firm* — Bolesh J. Skutnik; BJ Associates

(57) ABSTRACT

The present invention provides methods and compositions for increasing the effectiveness of photodynamic therapy ("PDT") and for reducing the duration of skin phototoxicity associated with PDT treatment. The disclosed methods generally include the administration of a lipid composition before, during, or after the administration of photosensitizers used in the PDT treatment protocol. The lipids are preferably phospholipids. It was discovered that the disclosed methods resulted in a more rapid clearance of photosensitizers from the skin and other tissue of patients, which results in a shorter period of skin phototoxicity after PDT treatment. The present invention also provides a composition which is preferably comprised of non-polar photosensitizers and phospholipids.

7 Claims, 4 Drawing Sheets

METHODS AND COMPOSITIONS FOR IMPROVING PHOTODYNAMIC THERAPY THROUGH ADMINISTRATION OF LIPIDS

DOMESTIC PRIORITY UNDER 35 USC 119(e)

This application claims the benefit of U.S. Provisional Application Ser. No. 60/543,984, filed Feb. 12, 2004, the contents of which are expressly incorporated herein by reference.

BACKGROUND OF THE INVENTION

1. Field of the Invention

The present invention relates to methods and formulations for improving photodynamic therapy (PDT). In particular the present invention relates to methods to reduce side-effects of PDT.

2. Information Disclosure Statement

Photodynamic therapy (PDT) is a well-accepted procedure for treating a variety of diseases and conditions. Of particular importance is PDT's success in fighting cancer, but it also has beneficial uses in many fields including various hyperproliferative skin conditions such as psoriasis, cosmetic hair removal, ocular disease treatments and wound treatment. PDT's usefulness is evident in its ability to selectively target diseased cells while leaving healthy cells unaffected.

PDT treatments generally consist of three steps. The first step involves systemically or locally introducing photosensitizers or their precursors to a patient. Systemic administration involves injection of the photosensitizer into the bloodstream, whereas local administration may involve the use of a cream or lotion for dermatological application. Photosensitizers, such as porphyrins or chlorins, exhibit the characteristic that they are nonreactive unless exposed to light of certain wavelengths. The next step involves allowing photosensitizers to preferentially accumulate around diseased tissue. Photosensitizers tend to be taken up by abnormally proliferative cells such as cancerous cells. After a sufficient period of time, the body flushes most of the photosensitizers, but proliferative cells retain them for a longer period. The result is that photosensitizers then substantially exist only in close proximity to abnormal cells. Photosensitizers applied locally generally require less time to accumulate with diseased tissue than those applied systemically. Finally, the site is to be treated with light of a suitable wavelength. This serves to activate the photosensitizers and produce cytotoxic effects. Because their destructive range is very small, the destructive effect is limited only to those cells that are close to the photosensitizers. Because only primarily cancerous or abnormally growing cells remain close to photosensitizers, these abnormal cells are destroyed and healthy tissue is spared.

Although PDT is an improvement over other treatments in many applications, and especially in cosmetic applications such as hair removal, it still suffers from some drawbacks. One major side-effect of photodynamic therapy is photosensitization of the skin and eyes after a full PDT treatment (i.e. application of photosensitizers and subsequent irradiation. As shown in FIG. 1, although the photosensitizer concentration in cancerous tissue becomes substantially greater than the concentration in other tissue, a significant concentration of photosensitizer remains in healthy tissue, such as the skin, for a substantial period of time after the photosensitizer is administered. If a patient is exposed to sunlight, indoor light, or any other light source that contains the activation wavelength, widespread and severe erythema can result. In such cases of systemic administration of photosensitizers, the patient's entire skin becomes photosensitized. In those cases where photosensitizers are topically applied, the area of skin that was treated will remain photosensitized. Patients must avoid sunlight and bright indoor light for up to 6 weeks or more to allow the photosensitizer to clear from the skin, and must wear protective clothing and sunglasses should they go outdoors during this period.

Efforts have been made to reduce the intensity and/or duration of skin hypersensitivity after photodynamic therapy. Where possible, the local administration of photosensitizers has been shown to limit skin photosensitivity to only limited areas of the skin. This method, however, is not effective for treatments that require systemic photosensitizer applications or applications over larger body areas. Additionally, local skin photosensitization is only effective if the photosensitive area can be easily shielded from bright light and sunlight. Local administration near the face or hands, for instance, would still pose a threat and be a major inconvenience to the patient.

Efforts have also been made to reduce the concentration of photosensitizer needed for a PDT treatment, so that less time is then required for the photosensitizer to clear from the skin. One way to reduce the needed concentration is to increase the specificity of the photosensitizers used in PDT. Photosensitizers have thus been conjugated with various molecules, such as target-specific antibodies, that are attracted to certain tissue.

Lipids are any of a heterogeneous group of fats and fatlike substances characterised by being water insoluble and being extractable by nonpolar solvents such as alcohol, ether, chloroform, and benzene. Lipids, which are easily stored in the body, serve as a source of fuel, are an important constituent of cell structure and serve other biological functions. Compound lipids comprise the glycolipids, lipoproteins and phospholipids. Phospholipids are the major structural lipids of most cellular membranes, and contain phosphate, usually as a diester.

Phospholipids have been utilized in various ways, such as in the manufacture of liposomes. Liposomes are submicron, hollow vesicles consisting of hydrated, synthetic phospholipids arranged in a bilayer structure. Attempts have been made to prepare formulations wherein non-polar, poorly water-soluble photosensitizers are encased in liposomes. (for example, see U.S. Pat. No. 6,074,666) Non-polar, hydrophobic photosensitizers include porphyrins, some porphyrin derivatives, chlorins (including benzoporphyrin derivative), purpurins, and phthalocyanines. Although these formulations may have use in aiding administration of photosensitizers, they do not substantially contribute to a reduction in PDT side-effects such as skin phototoxicity.

It would be extremely useful to have a composition and/or method that improves the pharmacokinetic properties of photosensitizers, as well as substantially reduces the severity and length of time of post-PDT skin photosensitization. The present invention addresses these needs.

OBJECTIVES AND BRIEF SUMMARY OF THE INVENTION

It is an object of the present invention to provide methods and compositions that increase the effectiveness and efficiency of photodynamic therapy ("PDT") treatments.

It is another object of the present invention to provide methods and compositions that increase the selectivity of photosensitizers used in PDT.

It is yet another object of the present invention to provide methods and compositions to reduce the side-effects of photodynamic therapy (PDT).

It is a further object of the present invention to provide methods and compositions to reduce the duration of skin phototoxicity after PDT.

Briefly stated, the present invention discloses methods and compositions for increasing the effectiveness of photodynamic therapy ("PDT") and for reducing the prolonged phototoxicity of the skin that results from PDT treatments. The methods generally consist of administration of a lipid composition before, during, or after administration of photosensitizers for photodynamic therapy. The lipids used are preferably phospholipids. Administration of a phospholipid formulation, incorporated into an existing PDT treatment protocol, has been found to result in a more rapid clearance of photosensitizers from the skin and other tissue of patients. This results in a shorter period of skin phototoxicity after PDT treatment. A formulation containing phospholipids, such as Lipofundin, is administered to a patient shortly before, during or after photosensitizers are administered for PDT. In another embodiment, a phospholipid formulation is applied prior to irradiation to improve the selectivity of the photosensitizers and reduce the interval between photosensitizer administration and irradiation. Also provided is a composition including non-polar photosensitizers and preferably phospholipids.

The above, and other objects, features and advantages of the present invention will become apparent from the following description read in conjunction with the accompanying drawings.

DETAILED DESCRIPTION OF PREFERRED EMBODIMENTS

Figure 1:
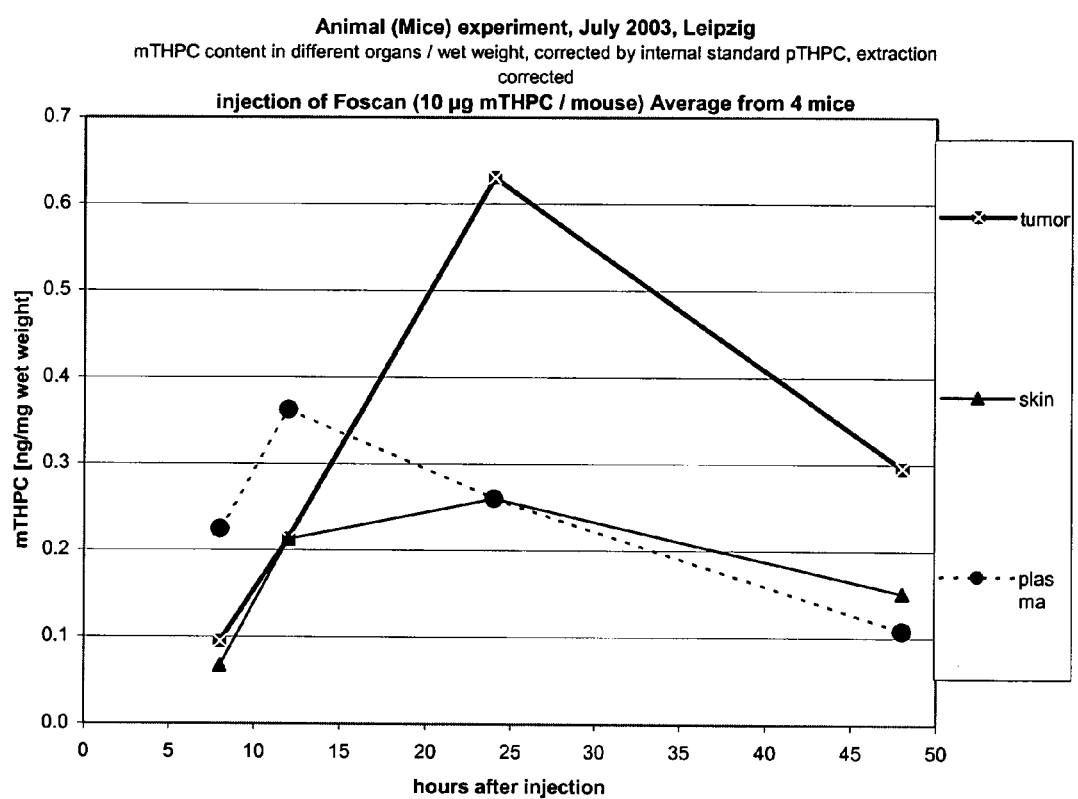
FIG. 1—Graph showing meta-tetra(hydroxyphenyl)chlorin ("mTHPC") concentration in tumor, skin and blood of a mouse after a dose of 10 μg mTHPC.

The present invention provides methods and formulations for improving photodynamic therapy ("PDT") and reducing side-effects associated therewith. A first general method involves application of lipids, preferably phospholipids, to a patient before, during or after PDT to increase the effectiveness of PDT by increasing the selectivity of photosensitizers and allowing for a reduction in the time needed between photosensitizer administration and irradiation (the "drug-light interval" or DLI). A second method involves administering lipids, preferably phospholipids, to a patient before, during or after PDT to quickly reduce the concentration of photosensitizers in a patient's skin due to photodynamic therapy (PDT). This method dramatically reduces the duration of post-treatment skin photosensitivity that is characteristic of normal PDT. Also provided is a formulation containing both photosensitizers and lipids for use in the above methods to improve PDT.

The present invention is ideally suited for PDT treatments that utilize non-polar, lipophilic photosensitizers. The solubility of such photosensitizers in lipids make them susceptible to removal from the skin using the present invention. A typical non-polar photosensitizer, having basic characteristics similar to most other non-polar photosensitizers, is meta-tetra(hydroxyphenyl)chlorin ("mTHPC"), also known as Temoporfin and by the trade name Foscan. This non-polar photosensitizer is described below in further detail as a typical example. A preferred modified PDT method of the present invention is as follows:

1) A photosensitizer formulation is administered to a treatment area of a patient, either locally to a specific tissue area, topically to a specific skin area, or systemically;
2) Sufficient time is allowed to elapse so that the photosensitizer preferably accumulates in diseased target tissue and concentrations in healthy tissue have been reduced to an acceptable level;
3) The treatment area is exposed to radiation having at least one wavelength suitable to activate the photosensitizer and render it cytotoxic. Because a higher concentration of photosensitizer is located in the diseased tissue, substantially only the diseased target tissue is destroyed by this process.
4) In a preferred embodiment, some time after the PDT treatment is complete, a formulation containing phospholipids is applied, preferably by intravenous injection or infusion, to the patient. For example, a phospholipid infusion approximately 5-10 hours after PDT (i.e. after both photosensitizer administration and subsequent irradiation) acts to quickly reduce skin photosensitizer concentration. In other embodiments, the phospholipid formulation is administered after photosensitizer injection but before irradiation, or may even be administered before photosensitizer administration in some instances. In further embodiments, administration of the phospholipid formulation may be performed more than once for a given PDT treatment, and may be performed any number of times both before, during or after photosensitizer administration or irradiation (for example, both before and after photosensitizer administration).

A preferred formulation containing phospholipids according to the present invention is Lipofundin® (B. Braun Melsungen AG). Lipofundin is a high-calorie nutritional source used by hospitals for patients who require parenteral nutrition. Lipofundin is an emulsion that includes soybean oil, medium-chain Triglyceride (MCT), and phospholipids from eggs.

In a preferred embodiment, PDT is performed as described above, and an infusion of Lipofundin is performed before, during or after photosensitizer administration or irradiation. The amount of Lipofundin applied is dictated by the normal use of Lipofundin; the dose is equal to the dose suggested for Lipofundin's standard uses (such as nutrition).

The timing, dose and frequency of phospholipid administration needed to reduce photosensitizer concentration in the skin will vary between photosensitizer, patient and treatment. Periodic skin fluorescence may be performed to determine the most desirable times, amounts and frequency of phospholipid administration. A fiber spectrometer is advantageously utilized to optimize the treatment.

The effectiveness of using phospholipids for reducing skin phototoxicity lies in the use of exchange equilibrium between plasma lipids (preferably phospholipids) and the photosensitizer in the skin, diluted in the skin lipids, to extract the photosensitizer from the skin. Because nonpolar photosensitizers, such as meta-tetra(hydroxyphenyl)chlorin ("mTHPC"), are highly soluble in lipids, the lipids introduced in the blood can act as a perfect solvent for mTHPC. Because of this solubility, the photosensitizers in the skin easily migrate to the blood; they are, in effect, washed out of the skin and into the bloodstream.

Normally, the lipid solution is continuously infused in the body over a period of hours. This is especially true for emulsions such as Lipofundin. This results in a longer period of time in which a higher level of phospholipids is present in plasma, during which the photosensitizer is effectively removed from the skin. A gradual infusion is more effective because the half life of phospholipids in plasma or blood is very short. In a preferred embodiment for Lipofundin, a standard infusion procedure (i.e. standard infusion periods for Lipofundin for nutritional or other accepted purposes) is used for applying the Lipofundin. The infusion procedure is begun preferably about 1-2 hours after PDT (i.e. after both administration of photosensitizer and irradiation).

The present invention can be used to reduce skin phototoxicity after local, topical or systemic photosensitizer administration. Obviously, the sensitization impact is greatest after systemic photosensitizer administration, due to the fact that the patient's entire skin area is sensitized after systemic photosensitizer application. Also, some non-polar photosensitizers must be administered systemically to be most effective. Skin sensitization on limited areas, such as after topical photosensitizer administration, is also beneficially affected by the present invention, especially for areas such as the face that are not easily or conveniently protected from light.

In addition to reducing skin phototoxicity after PDT, administration of phospholipids before, during, or shortly after (and preferably before irradiation) photosensitizer administration increases the effectiveness of PDT by improving photosensitizer selectivity and by reducing the drug-light interval. Because lipids or phospholipids aid in quickly removing photosensitizers from skin and other tissue, larger relative concentrations of photosensitizers can be achieved in target tissue (hyperproliferative tissue, including tumors and other cancerous tissue). This results in more efficient necrosis of the target tissue and reduces the risk of damaging healthy tissue. In addition, because the lipid formulation aids in quickly removing photosensitizers from healthy tissue, radiation can be applied more quickly after photosensitizer administration (reduced drug-light interval) than was possible in standard PDT.

A preferred method is similar to standard PDT methods, except that a formulation containing both photosensitizers (preferably non-polar) and lipids is administered to a patient. A period of time is allowed to elapse so that the photosensitizers preferentially accumulate in target tissue, followed by irradiation of the target tissue with a suitable wavelength. The presence of the lipids in the blood results in better accumulation of photosensitizers in target tissue relative to healthy tissue, and also reduces the drug-light interval compared to standard PDT. As described above, a preferred lipid formulation is a phospholipid formulation such as Lipofundin, and a preferred photosensitizer is meta-tetra(hydroxyphenyl) chlorin ("mTHPC"). A preferred shortened drug-light interval is between 6 and 8 hours.

The present invention can be used in conjunction with PDT using a variety of photosensitizers. In a preferred embodiment, application of lipids before, during or after PDT is preferred for those treatments that use non-polar, lipophilic photosensitizers. Such photosensitizers can be more quickly cleared from healthy skin and other healthy tissues by the addition of a lipid formulation, increasing the selectivity of PDT and reducing the drug-light interval. In addition, the skin concentration of any non-polar, poorly water soluble photosensitizer can be successfully reduced with the administration of a lipid formulation. Non-polar photosensitizers useful with the present invention include porphyrins, porphyrin derivatives (including benzoporphyrin derivative), chlorins, purpurins, phthalocyanines and metallo-derivatives thereof, dyes, and synthetic photo sensitizers.

meta-tetra(hydroxyphenyl)chlorin ("mTHPC"), also known as Temoporfin and by the trade name Foscan, is a photosensitizer shown to be effective in PDT of cancer, especially for advanced head and neck squamous cell carcinoma. The concentration of mTHPC has been shown to be substantially reduced in the skin after PDT by administration of phospholipids.

Figure 2:
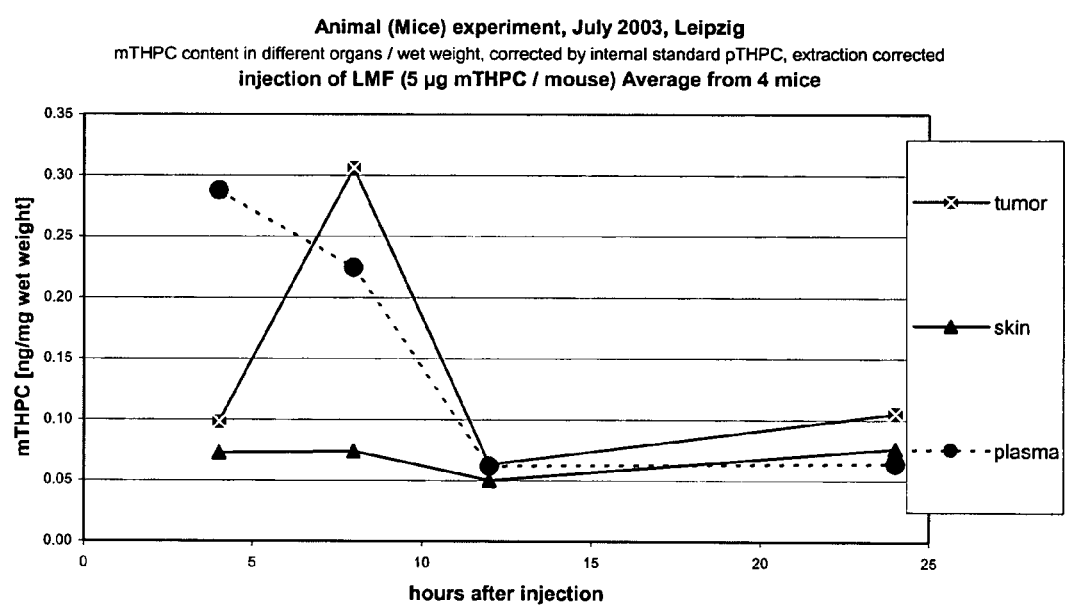
FIG. 2—Graph showing mTHPC concentration in tumor, skin and blood of a mouse after a dose of 5 μg mTHPC solubilized in Lipofundin MCT 10% ("LMF").

The effectiveness of the present invention is demonstrated by FIGS. 1 and 2. FIG. 1 shows the concentration of mTHPC in the skin, plasma, and tumors of mice after injection of mTHPC at a dose of 10 µg per mouse (hereinafter described as "Trial 1"). FIG. 2 shows the concentration of mTHPC in the skin, plasma, and tumors of mice after injection of a formulation of mTHPC (at a dose of 5 µg per mouse) solubilized in Lipofundin (hereinafter described as "Trial 2"). This formulation is abbreviated "LMF".

A number of significant advantages of the LMF formulation are evident. The first is that tumor concentrations of mTHPC increased much more rapidly during Trial 2 than during Trial 1. After only 8 hours, peak tumor concentration was achieved (0.31 ng/mg body weight) in Trial 2, whereas peak tumor concentration for Trial 1 was not observed until 24 hours. Indeed, after 12 hours, the tumor concentration in Trial 1 was only ⅔ that of the peak concentration in Trial 2.

Also, photosensitizer selectivity was demonstrably better after LMF injection than after mTHPC injection alone. At peak tumor concentration in Trial 2, which occurred at about 8 hours, the ratio of tumor concentration to skin concentration was about 4.4:1. In Trial 1, at peak tumor concentration occurring 24 hours after mTHPC injection, the ratio was only 2.4:1.

In addition, the level of photosensitizer concentration in the skin was much lower after LMF injection than after mTHPC injection alone, both in absolute and relative terms. In Trial 2 (LMF), the skin concentration stayed relatively steady at around 0.07 ng/mg. In contrast, the skin concentration in Trial 1 significantly increased to about 0.26 ng/mg after 24 hours, almost four times that of the skin concentration after LMF injection, even though the mTHPC dose of Trial 1 was only twice that of Trial 2.

Thus, as demonstrated above, the administration of lipids, particularly phospholipids, in conjunction with non-polar photosensitizers offers advantages such as shorter tumor uptake times resulting in shorter drug-light intervals, better tumor selectivity, lower skin photosensitizer levels, and reduced skin photosensitization.

In another preferred embodiment, both of the above methods are used in conjunction with a single PDT treatment to both increase the effectiveness of PDT and reduce skin phototoxicity after PDT. The following steps describe this combined method.

First, a composition containing both a non-polar photosensitizer and lipids (preferably phospholipids) is prepared.

Second, the composition is applied to a patient. Preferably, the formulation is administered by intravenous infusion.

Third, a period of time is allowed to elapse so that the photosensitizers accumulate in target tissue, such as cancerous cells, and allow the photosensitizers to be substantially cleared from the skin and other healthy tissue. Because of the exchange between the lipids in the blood and photosensitizers in body tissue, this period (drug-light interval) is observed to be shorter than the drug-light interval in standard (non-lipid) PDT.

Fourth, irradiation of a suitable wavelength is applied to destroy target tissue by activation of the photosensitizer.

Lastly, an additional lipid formulation is applied, preferably intravenously, to quickly reduce the concentration of photosensitizers in the skin and thus reduce the severity and duration of skin phototoxicity after PDT is complete. Administration of the lipid formulation is preferably administered as an infusion over time, to ensure a steady concentration of lipids in the blood. Also, numerous lipid administrations may be performed after PDT at various times.

Another object of the present invention is an improved photosensitizer-lipid formulation, wherein a photosensitizer formulation is combined with a lipid formulation to provide an improved formulation for PDT. Upon use of this formulation, both photosensitizers and lipids are simultaneously administered, and the lipids act to both improve the PDT treatment itself as well as reduce the duration of skin phototoxicity after PDT. For example, a "short infusion" of Lipofundin is performed wherein the overall dose of Lipofundin is 50 ml, and the infusion time is approximately 1 hour. Another example is consistent with more standard Lipofundin protocols, wherein the standard Lipofundin dose is 250 ml. The preferred infusion time is approximately 4 hours. These infusion times and doses are approximate and vary with body weight.

In a preferred embodiment, the formulation contains phospholipids and a non-polar, lipophilic photosensitizer. One example of a preferred formulation, described in more detail in Example 3 below, is a mTHPC-Lipofundin formulation.

The present invention is further illustrated by the following examples, but is not limited thereby.

Example 1

Injection of Lipofundin in Mice After Administration of mTHPC Photosensitizer

Figure 3:
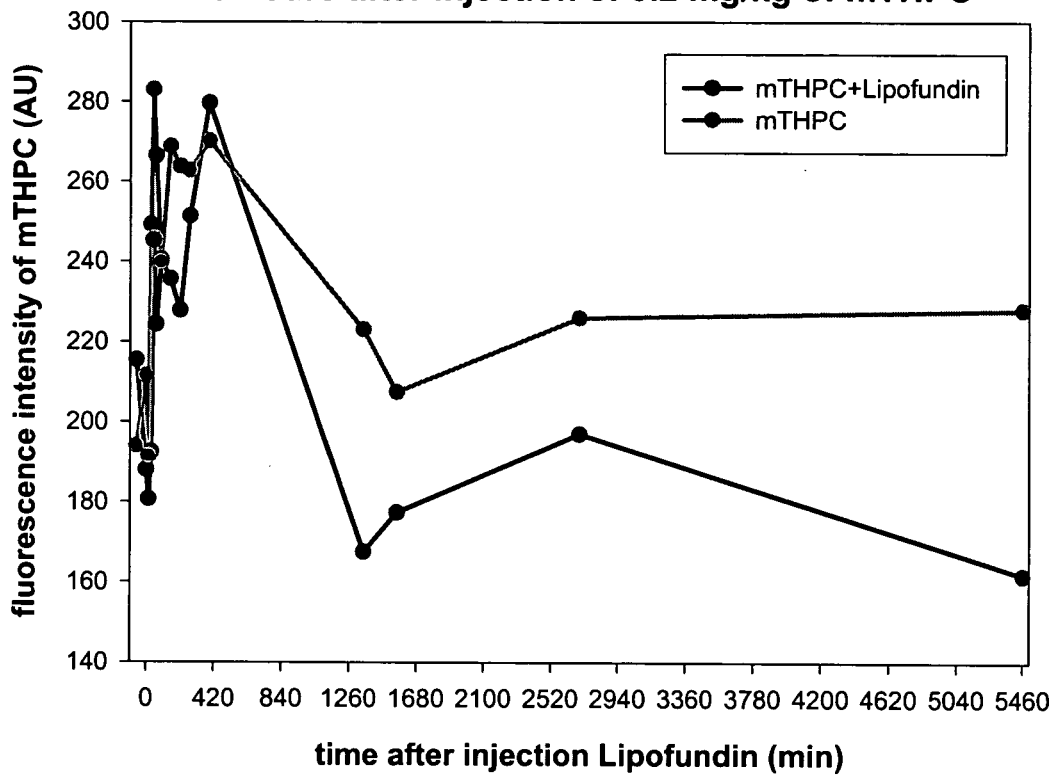
FIG. 3—Graph of results of skin fluorescence in a mouse after injection of Lipofundin 48 hours after mTHPC administration.

In this example, diluted meta-tetra(hydroxyphenyl)chlorin ("mTHPC") was injected into a mouse at a dose of 0.2 mg/kg body weight. After 48 hours (the time of peak mTHPC concentration in the tumor), a single bolus injection of 0.3 ml of Lipofundin® MCT ("Medium Chain Triglyceride")10% (B. Braun Melsungen AG) was performed. The point at which Lipofundin was administered is shown by "0" on the x-axis (time after injection). A bolus injection was required, because a continuous infusion of Lipofundin was not achievable in mice. Because the half live of the phospholipids in plasma in human is about 9 min, only a short period of high levels of plasma phospholipids could be reached in the mice. As is shown in FIG. 3, even though high levels of phospholipids were only achievable for a short time, it was enough to see a marked reduction in the skin fluorescence. Thus, even a small amount of phospholipids in the body for a short period can have a substantial effect on skin phototoxicity.

Example 2

Simultaneous Injection of Lipofundin and mTHPC in a Dog

Figure 4:
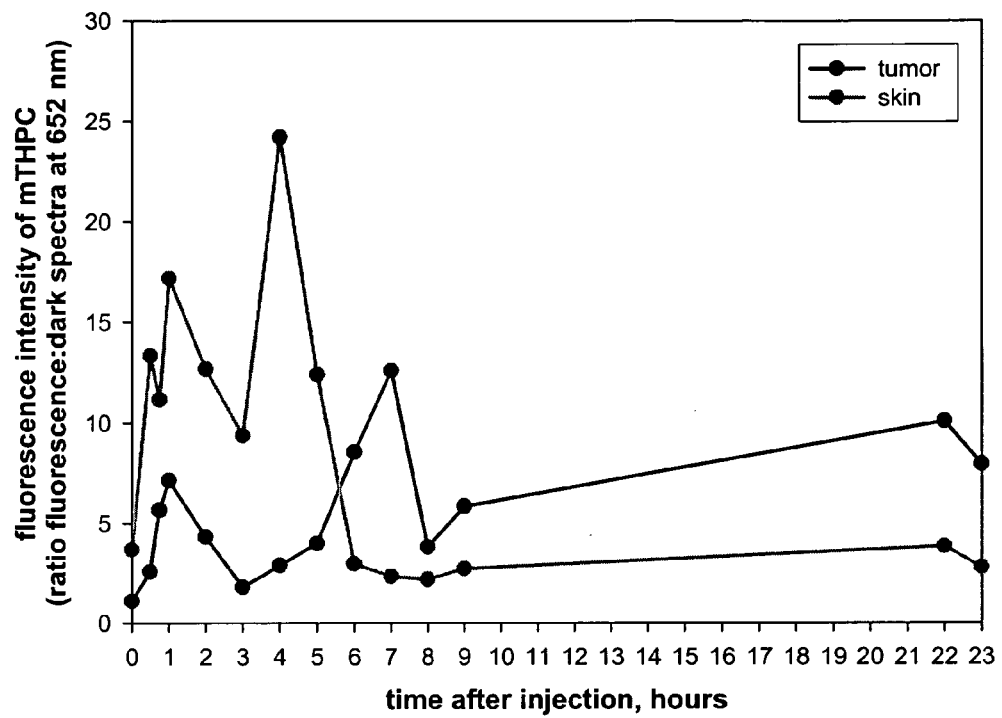
FIG. 4—Graph of results of skin fluorescence in sarcoma and skin of a dog after simultaneous injection of mTHPC and Lipofundin.

In this example, a standard mTHPC solution, having 4 mg of mTHPC per ml of solution (4 mg/ml), was diluted in Lipofundin until the concentration of mTHPC in the mixture is 0.75 mg/ml. The mixture was then injected, thus both the photosensitizer and phospholipids were simultaneously injected. The results of this simultaneous bolus injection are shown in FIG. 4, which demonstrates a rapid decrease in skin fluorescence and shows that the addition of phospholipids causes clearance of photosensitizer from the skin in a short time. As is shown in FIG. 4, after only 6 hours, the fluorescence of the skin was substantially the same as that measured prior to injection, thus the skin was no longer photosensitive after this short amount of time.

Example 3

Preparation and Use of a New mTHPC-Lipofundin Formulation

The following is an example of a suggested protocol for use by an authorized doctor or practitioner. The description covers the general details, but should not be considered a complete protocol, which would have to be expanded and approved by a national or regional regulatory authority.

This procedure describes the actions to be taken to prepare an infusion solution of mTHPC dissolved in Lipofundin MCT (10%) with a distinctly lower (but suitable) concentration of mTHPC (also known as temoporfin) inside the solution than in original mTHPC solutions, for immediate clinical use in infusion to treat distinct tumors by an authorized clinic. This procedure is only applicable for preparation of solutions from original standard mTHPC vials with a concentration of 4 mg/ml.

This procedure applies to materials and procedure used for the dilution of mTHPC in Lipofundin for direct clinical use of lower concentration solutions of mTHPC than have been produced to date by biolitec Pharma Ltd. and approved by the EMEA (European agency for the evaluation of medicinal products).

Suggested Materials are as Follows:
I) Compounds
   Original vial(s) of mTHPC solution
   Original bottle/s Lipofundin MCT (10%)
II) Other Materials
   Suitable brown sterile bottles for mixing and storing—only with method A ("short time infusion")
   Suitable sterile brown infusion bottles for storage of the final diluted solution, with suitable closures and closing instruments—only with method A ("short time infusion")
   Sterile measuring cylinder, size 50 ml—only with method A ("short time infusion")
   Sterile disposables such as syringes for precise volumetric measurement of 0.5 ml up to 5 ml at least
   Injection filters
   1.2 μm pore size infusion filter
   Variable infusion pump
Procedure for Preparation of a Diluted Solution of mTHPC in Lipofundin:
1) Calculation of mTHPC Content:
   Calculate the appropriate amount of mTHPC needed for administration to the patient depending on the patient's body weight. Refer to an authorized document where the application and dosage is described.
2) Dilution of mTHPC in Lipofundin MCT 10%:
A) Dilution for Short Time Infusion:
   Prepare a sterile container for mixing and storing the preparation. Add 50 ml of Lipofundin to the container. Take the calculated amount (see point 1.) from an original mTHPC solution vial using a sterile syringe. When calculating the amount, the dead space volume that is represented by the volume of the infusion set should be considered. With e.g. 5 ml dead space volume and 50 ml Lipofundin being used, it must be considered that only 45 ml will be infused. Thus, the whole amount of mTHPC to be administered must be contained in 45 ml. Inject the amount of mTHPC into the prepared bottle with Lipofundin under gentle agitation over a period of 3 min. Transfer the mixture to a sterile empty bottle for infusion of appropriate size. Close the bottle with sterile closure before transferring into nonsterile conditions and using for infusion. Always follow sterile working rules.

B) Dilution for Standard Infusion

Prepare a ready to use original flask of Lipofundin MCT 10% (usually 250 ml). Take the calculated amount (see point 1.) from an original mTHPC solution vial using a sterile syringe. When calculating the amount, the dead space volume that is represented by the volume of the infusion set should be considered. With e.g. 5 ml dead space volume and 250 ml Lipofundin being used, it must be considered that only 245 ml will be infused. Thus, in 245 ml the whole amount of mTHPC to be administered must be contained. Inject the amount of mTHPC into the original Lipofundin flask under gentle agitation over a period of 3 min. Always follow sterile working rules.

The addition of original mTHPC must be performed in any case with the injection filter (or corresponding) that is used for original mTHPC application and delivered with it.

According to FDA guidelines for infusion of lipid emulsions, the infusion must be done using a 1.2 μm pore size infusion filter. Because of the viscosity of the Lipofundin mixture, use of an active infusion with an infusion pump, while not mandatory, is recommended. Manual pressure can also be used, especially for the short time infusion.

Example 4

Influence of Intravenous Administration of Lipid Emulsion Following Irradiation

This example demonstrates the influence of Lipofundin intravenous administration on Foscan pharmacokinetics using data generated from a clinical trial.

Experimental Group

Ten patients (6 male, 4 female) with basal-cell cancer (BCC) of the skin were treated with Foscan PDT course having a drug dose of 0.05 mg/kg, a drug-light interval 48 hours, and a 50 J/cm$^2$ light dose. Immediately after the laser treatment these patients were given intravenous drop infusions of 10% Lipofundin (250 ml). Patients were administered a second infusion of 10% Lipofundin solution (250 ml) the next day.

Control Group

A group of ten patients (6 male, 4 female) with BCC of the skin, were administered Foscan PDT course having a drug dose of 0.05 mg/kg, a drug-light interval 48 hours, and a 50 J/cm$^2$ light dose. No 10% Lipofundin infusions were administered post-irradiation.

Post-administration Monitoring of Foscan Fluorescence

A computer-based spectrometer Optical Biopsy System (OBS) specially tuned for clinical monitoring of skin fluorescence was used to detect and measure skin fluorescence. The OBS uses a 400 nm diode laser to induce FOSCAN fluorescence (wavelength 655 nm) which is then detected and measured by the OBS spectrometer.

Fluorescence measurements were performed in intact skin of the cheek at certain time points after Foscan injection. Fluorescence monitoring began 2 days after Foscan administration and was continued for 7 weeks following Foscan administration. All measurements were performed by using contact tip (FD-1 Handstuck). Each fluorescence measurement was performed 4 times, all results were recorded, and the average value was used for further analysis.

The observed dynamics of Foscan fluorescence in both groups are summarized below in Table 1. The data show that the Experimental Group exhibits a more rapid decrease in skin fluorescence (i.e. more patients having no detectable fluorescence) as compared to the Control Group, which suggests that the administration of lipids following PDT treatment contributes to faster elimination or clearance of photosensitizers from the tissue and reduces the duration of PDT associated skin phototoxicity for the patient.

TABLE 1

Comparison of Foscan fluorescence dynamics in Experimental and Control groups as detected by OBS

| | Number of patients exhibiting no detectable skin fluorescence as detected by OBS Number of days after Foscan application | | | | |
|---|---|---|---|---|---|
| | 7 | 14 | 21 | 28 | 35 |
| Experimental Group | 0 | 2 | 5 | 10 | 10 |
| Control Group | 0 | 0 | 2 | 7 | 10 |

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method of photodynamic therapy comprising the steps of:
   a) administering a lipophilic photosensitizer to a treatment area in a patient;
   b) at a suitable time after step a), irradiating said treatment area with radiation having at least a wavelength suitable to activate said photosensitizer to destroy target tissue in said treatment area; and
   c) following irradiation of the treatment area, administering a formulation comprising a lipid emulsion to the patient.

2. The method of claim 1, wherein the formulation comprising said lipid emulsion is administered at least 5 hours following irradiation of the treatment area.

3. The method of claim 2, wherein the formulation comprising said lipid emulsion is administered between 5 and 10 hours following irradiation of the treatment area.

4. The method of claim 3, wherein the formulation comprising said lipid emulsion is Lipofundin.

5. The method of claim 1, wherein said lipid emulsion comprises soybean oil, medium-chain triglycerides, and phospholipids from eggs.

6. The method according to claim 1, wherein said lipid emulsion includes phospholipids as a component of the formulation.

7. The method according to claim 1, wherein said lipophilic photosensitizer is selected from the group consisting of porphyrins, phthalocyanines, metallo derivative thereof, dyes, and synthetic photosensitizers.

* * * * *